US009709686B2

United States Patent
Bradford et al.

(10) Patent No.: US 9,709,686 B2
(45) Date of Patent: Jul. 18, 2017

(54) MODULAR POSITRON EMISSION TOMOGRAPHY (PET) GANTRY

(71) Applicant: General Electric Company, Schenectady, NY (US)

(72) Inventors: Robert George Bradford, Waukesha, WI (US); Rajender Singh, Bangalore (IN); Rahul Raghavan, Bangalore (IN); Timothy Patrick Rose, Waukeska, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 14/630,127

(22) Filed: Feb. 24, 2015

(65) Prior Publication Data

US 2016/0187496 A1    Jun. 30, 2016

(30) Foreign Application Priority Data

Dec. 30, 2014    (IN) .......................... 6735/CHE/2014

(51) Int. Cl.
*G01T 1/29*       (2006.01)
*G01T 7/00*       (2006.01)
*A61B 6/03*       (2006.01)

(52) U.S. Cl.
CPC ............ *G01T 1/2985* (2013.01); *A61B 6/037* (2013.01)

(58) Field of Classification Search
CPC ........ G01T 1/2985; G01T 1/1644; G01T 7/00
USPC ...... 250/363.03, 363.02, 361 R, 363.04, 366
See application file for complete search history.

(56) References Cited

U.S. PATENT DOCUMENTS

| | | | | |
|---|---|---|---|---|
| 3,379,032 A | * | 4/1968 | Wilson .................. | E21B 47/011 165/135 |
| 5,825,031 A | * | 10/1998 | Wong ...................... | G01T 1/164 250/363.03 |
| 7,102,134 B2 | * | 9/2006 | Weinberg .............. | A61B 6/0414 250/363.02 |
| 7,525,097 B2 | | 4/2009 | Dorscheid et al. | |
| 2001/0040219 A1 | * | 11/2001 | Cherry .................... | G01T 1/202 250/363.03 |
| 2002/0056809 A1 | * | 5/2002 | Frederick ................. | G01V 5/06 250/361 R |
| 2005/0094763 A1 | * | 5/2005 | Sherman ................. | A61B 6/032 378/19 |
| 2005/0231025 A1 | * | 10/2005 | Yasumura ........... | B60B 27/0005 301/105.1 |

(Continued)

FOREIGN PATENT DOCUMENTS

CN         103549966 A        2/2014

OTHER PUBLICATIONS

Search Report and Written Opinion from corresponding PCT application No. PCT/US/2015/053080 dated Jan. 14, 2016; 18 pages.

*Primary Examiner* — David Porta
*Assistant Examiner* — Blake Riddick
(74) *Attorney, Agent, or Firm* — Dean D. Small; The Small Patent Law Group, LLC

(57) ABSTRACT

A modular PET gantry is provided herein. A detector module is described, and the detector module includes a plurality of PET detector units. Each detector unit may be bonded to a mounting sleeve. The detector module also includes a mounting frame, wherein each detector unit and mounting sleeve is attached to the mounting frame.

20 Claims, 10 Drawing Sheets

(56) References Cited

U.S. PATENT DOCUMENTS

| | | | |
|---|---|---|---|
| 2007/0080296 A1* | 4/2007 | Ueno | G01T 1/2985 250/363.04 |
| 2009/0179153 A1* | 7/2009 | Del Medico | G01T 1/1642 250/363.04 |
| 2010/0264320 A1* | 10/2010 | Takayama | A61B 6/037 250/362 |
| 2011/0240864 A1 | 10/2011 | Degenhardt et al. | |
| 2012/0112078 A1* | 5/2012 | Millett | G01T 1/1612 250/363.03 |
| 2013/0119259 A1* | 5/2013 | Martin | G01T 1/1648 250/363.03 |
| 2013/0256537 A1 | 10/2013 | Laurence et al. | |
| 2014/0361181 A1 | 12/2014 | Liu | |
| 2014/0367577 A1* | 12/2014 | Badawi | A61B 6/037 250/366 |

\* cited by examiner

200

400A

400B

400D

500

MODULAR POSITRON EMISSION TOMOGRAPHY (PET) GANTRY

BACKGROUND OF THE INVENTION

Nuclear medicine is a medical specialty where a radiopharmaceutical is introduced to a patient to identify and treat disease. The radiopharmaceutical causes the emission of photons from the body of the patient, and can concentrate in particular tissues of the body, indicating tissue metabolic activity at the site of concentration and emitting a higher amount of photons from the site of concentration. Images may be reconstructed from the photons observed during Positron Emission Tomography (PET).

In particular, a plurality of detectors of a PET system may be used to observe the photons that occur in a coincident event. The detectors are typically positioned in a ring formation, with the patient supported by a table and positioned within the ring. During manufacture, the detectors are permanently bonded in groups of detectors and then mounted in the ring formation. When a single detector unit of a group of detectors fails, the entire grouping is removed and replaced. This results in wasted materials and labor.

SUMMARY OF THE INVENTION

An embodiment relates to a modular PET gantry. A detector module is described, and the detector module includes a plurality of PET detector units. Each detector unit may be bonded to a mounting sleeve. The detector module also includes a mounting frame, wherein each detector unit and mounting sleeve is attached to the mounting frame.

Another embodiment relates to a detector unit. The detector unit includes: a detection tube and a scintillator block. A light guide is to guide scintillations from the scintillator block to the detection tube, and a mounting sleeve is to enable location and mounting features of the detector unit.

Still another embodiment relates to a modular PET system. The modular PET system includes a plurality of detector modules, a plurality of detector units, and a mounting frame. The detector modules are arranged in a ring, and each detector module includes a plurality of PET detector units. Each detector unit is bonded to a mounting sleeve. Each detector module also includes a mounting frame, wherein each detector unit and mounting sleeve are attached to the mounting frame.

BRIEF DESCRIPTION OF THE DRAWINGS

The present techniques will become more fully understood from the following detailed description, taken in conjunction with the accompanying drawings, wherein like reference numerals refer to like parts, in which.

In some cases, the same numbers are used throughout the disclosure and the figures to reference like components and features. Numbers in the 100 series refer to features originally found in FIG. 1; numbers in the 200 series refer to features originally found in FIG. 2; and so on.

DETAILED DESCRIPTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

As discussed above, current scanners in nuclear medicine do not enable any modularity. In the embodiments discussed herein, a modular PET gantry is disclosed that enables the installation and removal of individual PET detector units while still enabling precise mounting of detector units to obtain a high quality PET scan. The installation or removal of detector units can be completed in a manufacturing facility or in the field after the scanner has been installed.

A technical effect of at least one embodiment is a mounting sleeve bonded to a detection tube. In embodiments, the light guide is to guide scintillations from a scintillator block to the detection tube. Further, another technical effect of at least one embodiment includes a modular design that enables an accurate and precise positioning of PET detectors within PET-CT scanner to support consistent, high-quality images. Multiple fields of view are possible depending on the number of rows of detectors that are populated onto a ring structure of the PET system, thus offering multiple product configurations on the same platform. Further, replacement of individual detectors may occur during manufacturing or at a customer site by a service technician. An existing modular system can be upgraded from a lower field of view to a higher field of view during manufacturing staging or at the customer site.

Figure 1A:
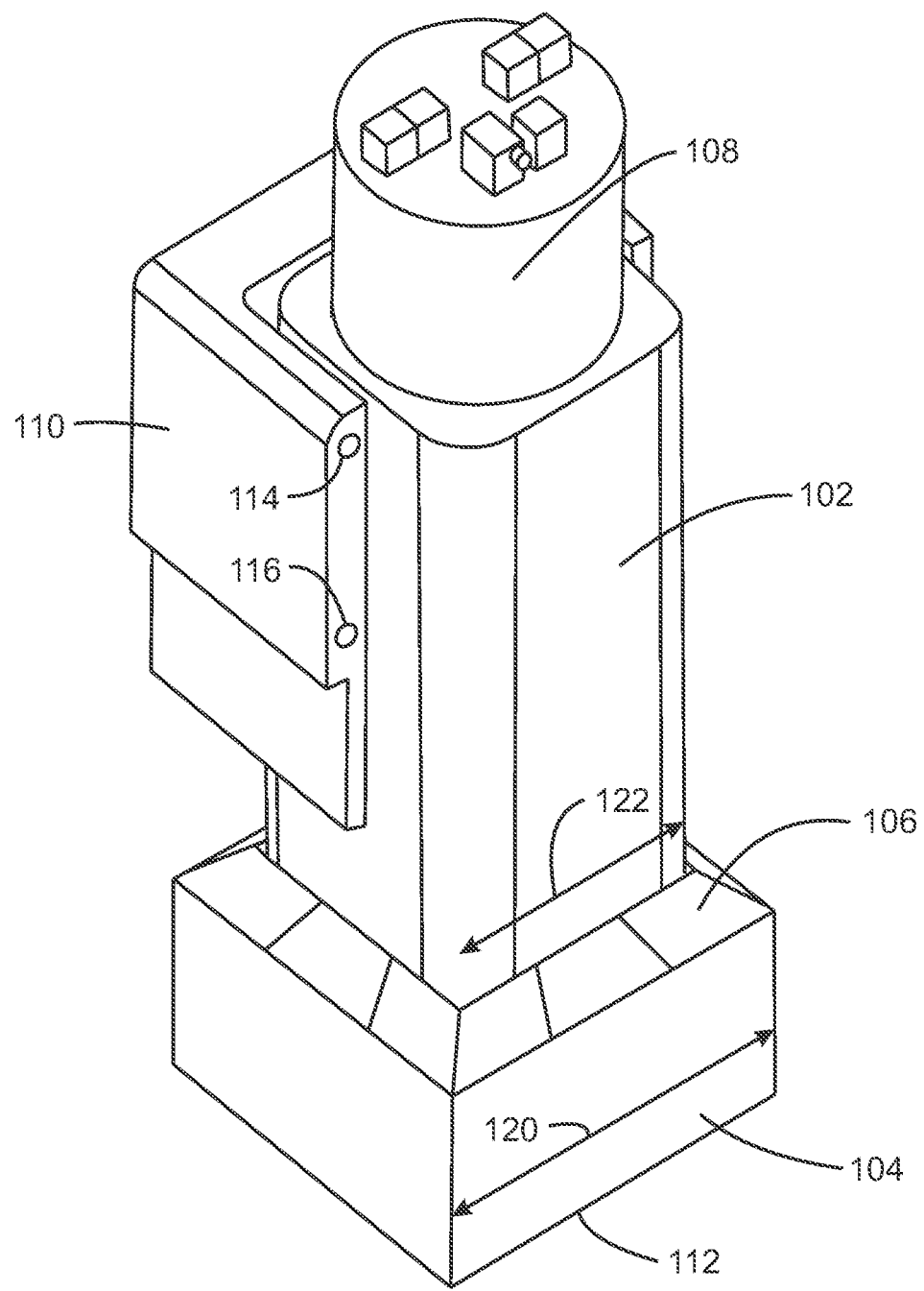
FIG. 1A is an illustration of a detector unit in accordance with embodiments.

In FIG. 1A, a detector unit 100 is depicted in accordance with an embodiment. In embodiments, the detector unit 100 is a photomultiplier tube detector unit. Accordingly, the detector unit 100 includes a detection tube that is a photomultiplier (PMT) tube 102 coupled to a scintillator block 104. During operation, the scintillator block 104 is to receive radiation, such as gamma radiation (gamma rays), from a patient during a Positron Emission Tomography (PET) scan. The various embodiments are not limited to medical imaging systems for imaging human subjects, but may include, for example, veterinary systems. As used herein, the term "patient" may refer to a human patient or any other animal. The scintillator block 104 may include a number of crystals that emit light or fluoresce in response to excitation from the gamma rays. The PMT tube 102, coupled to the scintillator block 104, acquires this light from the scintillator block 104. The PMT tube 102 can detect very low levels of scintillation, and cascade the signal up the length of the PMT tube 102 in order to generate an amplified analog or digital signal that is obtained by electric circuitry of the PET gantry via a connectivity module 108. This signal is used by software of the PET gantry in order to generate an image of functional processes in the body of the patient.

Traditionally, to generate high quality PET scans, a width of the scintillator block and a width of a PMT tube were equal to ensure that each photon emitted by the scintillator block is acquired by the PMT tube. This results in a one-to-one ratio between the width of the scintillator block and a width of the PMT tube. This one-to-one correspondence has traditionally limited dimensions of the PMT tube by the dimensions of the scintillator block. In embodiments, a width 120 of the scintillator block 104 is greater than a width 122 of the PMT tube 102. As used herein, the width 120 of the scintillator block 104 compared to the width 122 of the PMT tube 102 may be referred to as an aspect ratio. In embodiments, the aspect ratio is approximately four-to-three, making the width of the tube small enough to accommodate a mounting sleeve. Thus, the aspect ratio of the detector unit enables accommodation of a mechanical mounting sleeve. A light guide 106 is able to guide the output of the scintillator block 104 into the PMT tube 102, without losing any light emitted by the scintillator block 104.

In embodiments, the detector unit 100 includes a mounting sleeve 110. The mounting sleeve is bonded to the PMT tube 102. The mounting sleeve 110 is a precision manufactured sleeve. The detector unit 100 is bonded to the mounting sleeve 110 using a gluing fixture. The gluing fixture is a precision manufactured locating fixture which locates the mounting sleeve 110 accurately and precisely relative to the remainder of the detector unit 100 during the gluing/curing process. This ensures that the mounting features of the sleeve are correctly located relative to scintillator block 104, which in turn, ensures the scintillator block 104 is correctly located in three dimensional space onto a detector frame, sufficient to generate a high-quality image. In embodiments, the glue is a silicon based adhesive used for PET detector bonding applications.

Figure 1B:
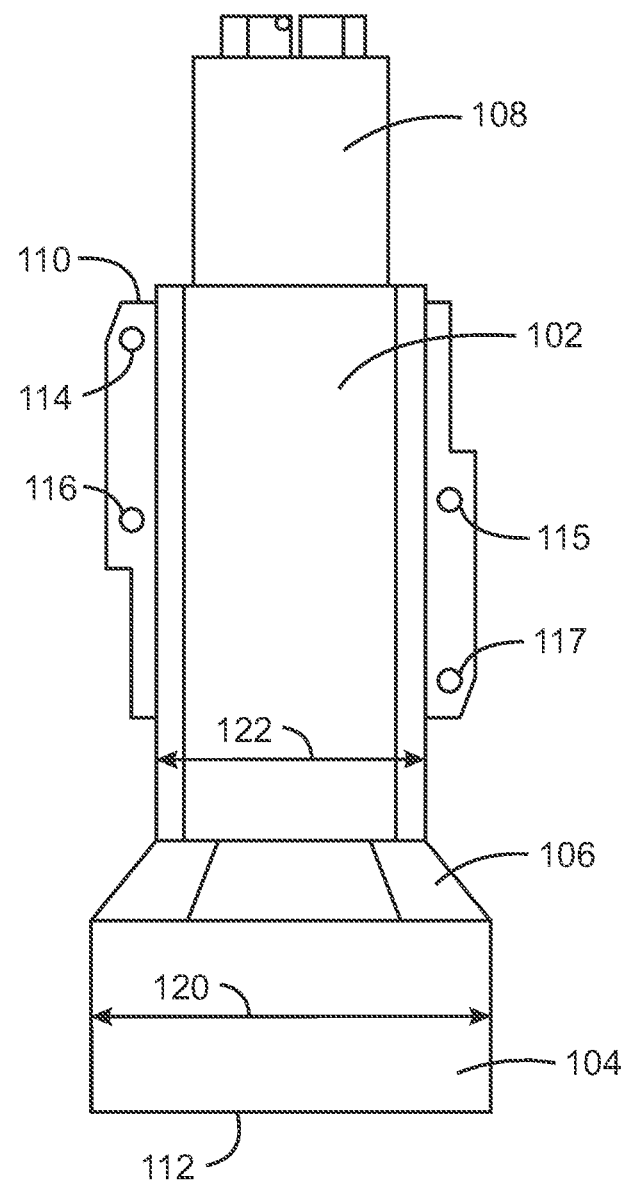
FIG. 1B is an additional view of a detector unit in accordance with embodiments.

The mounting sleeve 110 is to ensure the detector unit 100 is precisely mounted and located in a mounting frame with respect to other detector units. A face 112 of the scintillator block 104 is the primary locating datum of the detector unit 100 within the gluing fixture. The face 112 of the scintillator block 104 is located at the base of the detector unit 110, and is not visible in FIG. 1. The face 118 of the scintillator block 104 is located on side surface and is not shown in FIG. 1. The face 119 of the scintillator block 104 is located on front face as shown in FIG. 1. Using the face 112, face 118 and face 119 of the scintillator block 104 as the primary, secondary and tertiary locating datums, results in the scintillator block 104 being well located with respect to the mounting sleeve. This ensures a high quality PET scan, as the scintillator block 104 detects the gamma rays during a PET scan and error in the location of the scintillator block 104 results in error in the final image generated during the PET scan. The mounting sleeve 110 itself is located for bonding via precision molded or machined pin-hole features within the mounting sleeve 110, which rest on locating pins on the gluing fixture. In FIG. 1, the locating pins on the gluing fixture and the gluing fixture are not visible, as the locating pins and gluing fixture for bonding the mounting sleeve 110 to the PMT tube 102 are behind the PMT tube 102. The mounting sleeve 110 also includes holes 114 and 116. The holes 114 and 116 can be used to align the detector unit 100 onto a mounting frame. Additional holes 115 and 117 are visible in FIG. 1B.

FIG. 1B is another view of the detector unit 100. As described above, the detector unit 100 includes a PMT tube 102 coupled to a scintillator block 104 via light guide 106. Detector unit 100 also includes a connectivity module 108 as part of photon multiplier tube 102. The aspect ratio of the detector unit 100 is approximately four-to-three. A light guide 106 is able to guide the output of the scintillator block 104 into the PMT tube 102, with minimal loss of light emitted by the scintillator block 104.

The mounting sleeve 110 includes holes 114, 115, 116, and 117. The holes 114, 115, 116, and 117 can be used to align the detector unit 100 onto a mounting frame. In embodiments, the holes 114 and 117 are pin holes that are used for pin locating and can mate with pins on a frame. The holes 115 and 116 may be two thru holes for use with a screw, and can align with additional holes on a frame. In embodiments, two pins are to enable control of the location and rotation of the detector unit prior to securing the detector unit with two screws.

Figure 2:
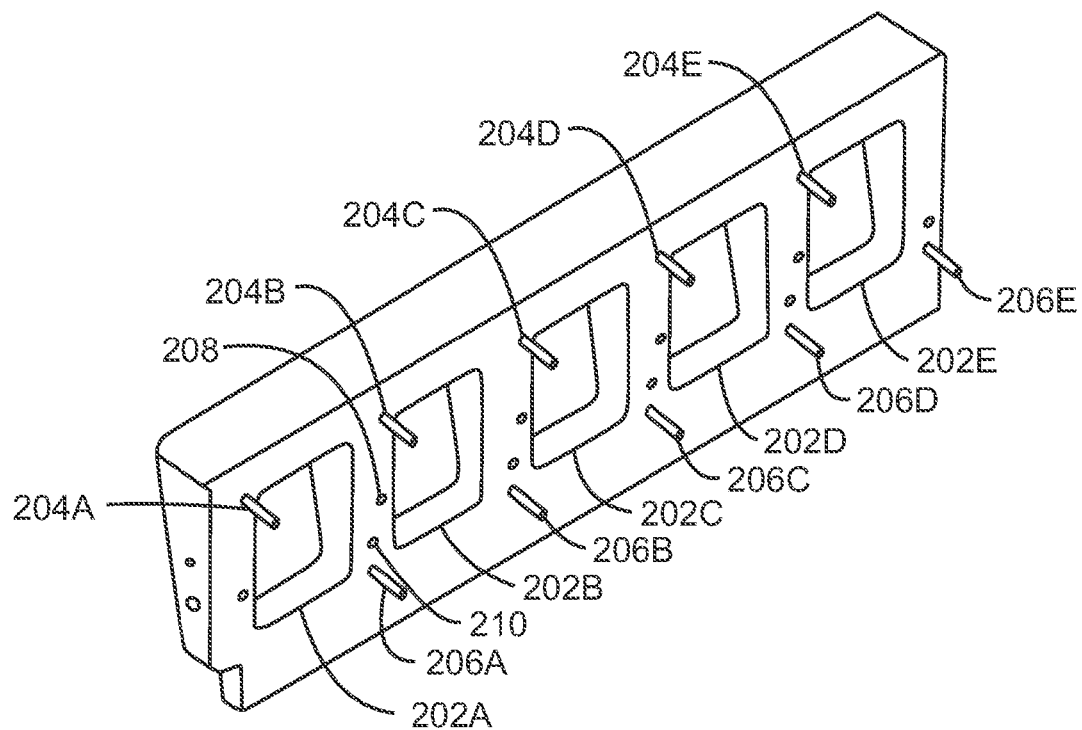
FIG. 2 is an illustration of a mounting frame in accordance with embodiments.

FIG. 2 is an illustration of a mounting frame 200 in accordance with embodiments of the present techniques. The mounting frame 200 includes a plurality of sites 202. In particular, each site 202A, 202B, 202C, 202D, and 202E are created to reduce the weight of mounting frame 200. The surface area 207 on a mounting frame as shown in FIG. 2 provides mounting support for a detector unit. The surface area 208 on mounting frame provides support for a detector frame on opposite side and not shown in FIG. 2. Thus, the mounting frame 200 can receive a plurality of detector units. A mounting frame populated with any number of detector units is a detector module. While five sites are illustrated in FIG. 2, the mounting frame may include any number of sites to reduce mounting frame weight. Moreover, the sites can be located at any position along the mounting frame. For example, sites can be located along both a front surface and a rear surface of the mounting frame 200.

The mounting frame 200 generally includes a plurality of pins 204 and a plurality of pins 206 corresponding to the plurality of sites 202. Thus, site 202A includes pins 204A and 206A, site 202B includes pins 204B and 206B, and so on. Generally, each of pin 204 and pin 206 are able to receive a mounting sleeve, such as the mounting sleeve 110 (FIG. 1A and FIG. 1B). The pin 204 and the pin 206 ensure that the mounting sleeve is precisely located at each site 202 of the frame 200. In this manner, the mounting sleeve of the detector unit is precisely located with respect to the frame. In embodiments, the pin 204 and the pin 206 may mate with at least one of a pin hole 114 or pin hole 117 of detector unit 100. Additionally, holes in the frame may correspond to holes in a mounting sleeve. For example, a hole 208 and a hole 210 may also correspond to holes in the mounting sleeve 110, such as hole 115 or hole 116. The hole 208 and a hole 210 may be machined to receive a locking mechanism, such as a screw, in order to secure the mounting sleeve in a proper position with respect to the mounting frame 200 through each of holes.

Accordingly, the mounting frame 200 includes various precision location features that enable each detector unit to be precisely and accurately located with respect to other detector units attached to the mounting frame 200. The precise and accurate location features enable accurate image registration when using a detector module to perform a PET scan. Although FIG. 2 is illustrated with a particular number of pins and holes, each mounting frame can include any number of pins and holes. Moreover, each site can include a differing number of pins and holes, and the mounting sleeve may be designed to receive any number of pins and holes. The number of pins and holes in the mounting sleeve may depend on the design of the mounting frame. Further, while the pins, pin holes, and holes are illustrated in the mounting sleeve 110 and the mounting frame 200 at certain positions, these locations are exemplary and can be located at any position along the mounting sleeve 110 and the mounting frame 200.

In an example, a detector unit can be configured to attach to a mounting frame, where the mounting frame can hold up to five rows of two detector units. Each detector unit is individually located onto the frame via locating pins pre-installed into the frames. The locating pins 204 may be individual pin that extends on side of the mounting frame as shown in FIG. 2. In another embodiment, the locating pins 204 may be the same pin that extends from a front side of the mounting frame to the rear side of the mounting frame. By using the precise location and orientation of locating pin, mechanical tolerances that may accumulate from several individual detector units and the mounting frame is minimized Thus, a total of stacked tolerances are minimized in the detector module. Once located using the pins, each detector unit is secured using screws or other locking mechanism. The interface between the mounting sleeve and the mounting frame enables modularity of a PET gantry built using detector units as described herein. In particular, each unit can be individually removed or replaced without impacting the neighboring units. Further, proper image registration when an individual detector unit is removed or replace is maintained.

Figure 3:
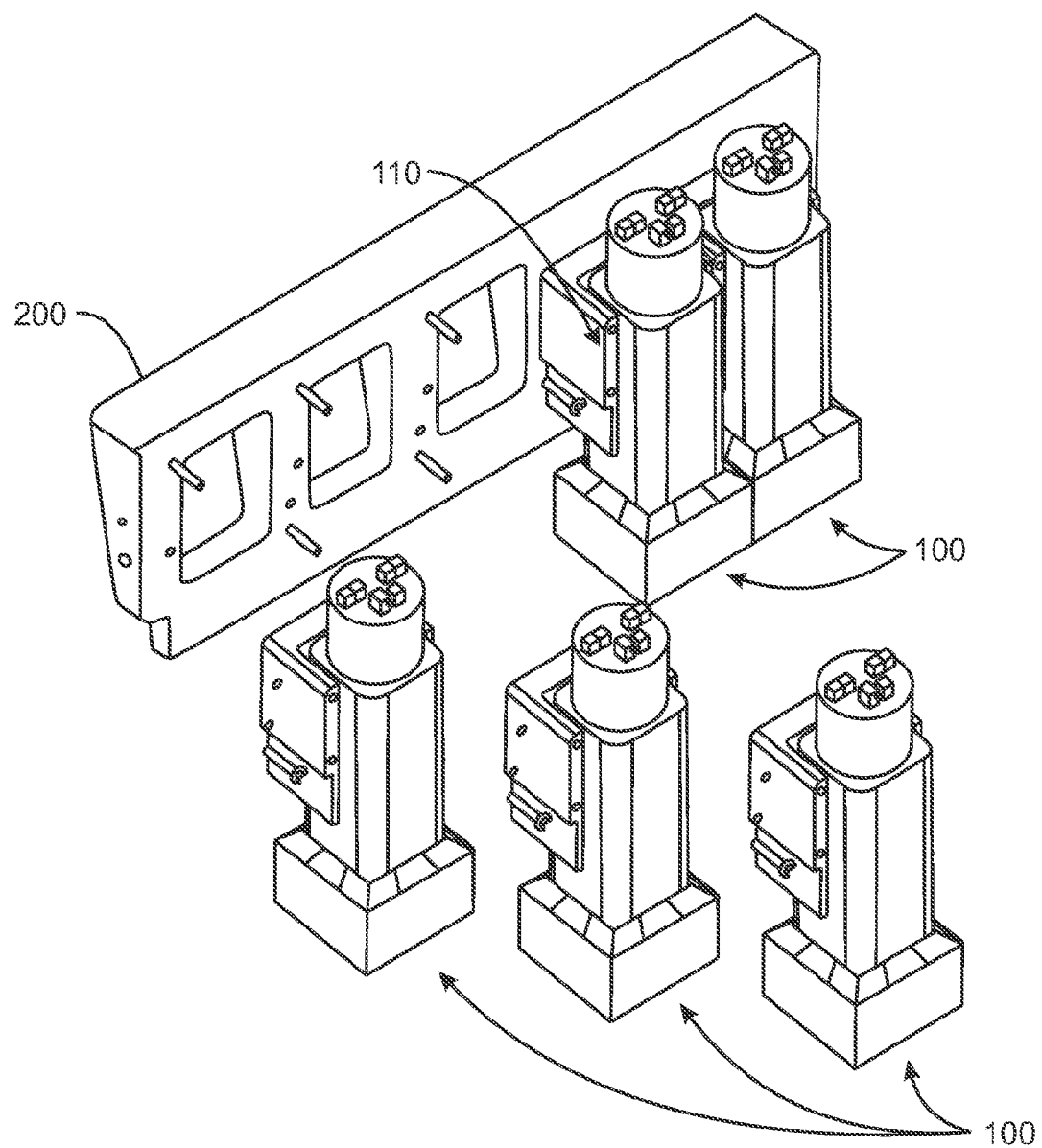
FIG. 3 is an exploded view of a detector module in accordance with embodiments.

FIG. 3 is an exploded view of a detector module 300 in accordance with embodiments. Five detector units 100 are illustrated in various stages of attachment to the mounting frame 200. Each detector unit includes a mounting sleeve that is to releasably attach to the mounting frame 200 to form the detector module 300. Although the present techniques are described using precision locating features such as alignment pins and screw holes, other techniques may be used to ensure the precise and accurate location of the detector unit as attached to the mounting frame. For example, a rail system may be machined onto the mounting frame. In such an example, the mounting sleeve would include components to enable the mounting sleeve to slide into a railing system of the mounting frame. The mounting sleeve may also slide into and lock into the railing system. In another example, a pocket or holster may be machined onto the mounting frame. In this example, the mounting sleeve may be formed in such a manner where is it to drop and lock into the pocket or holster created by the mounting frame.

Figure 4A:
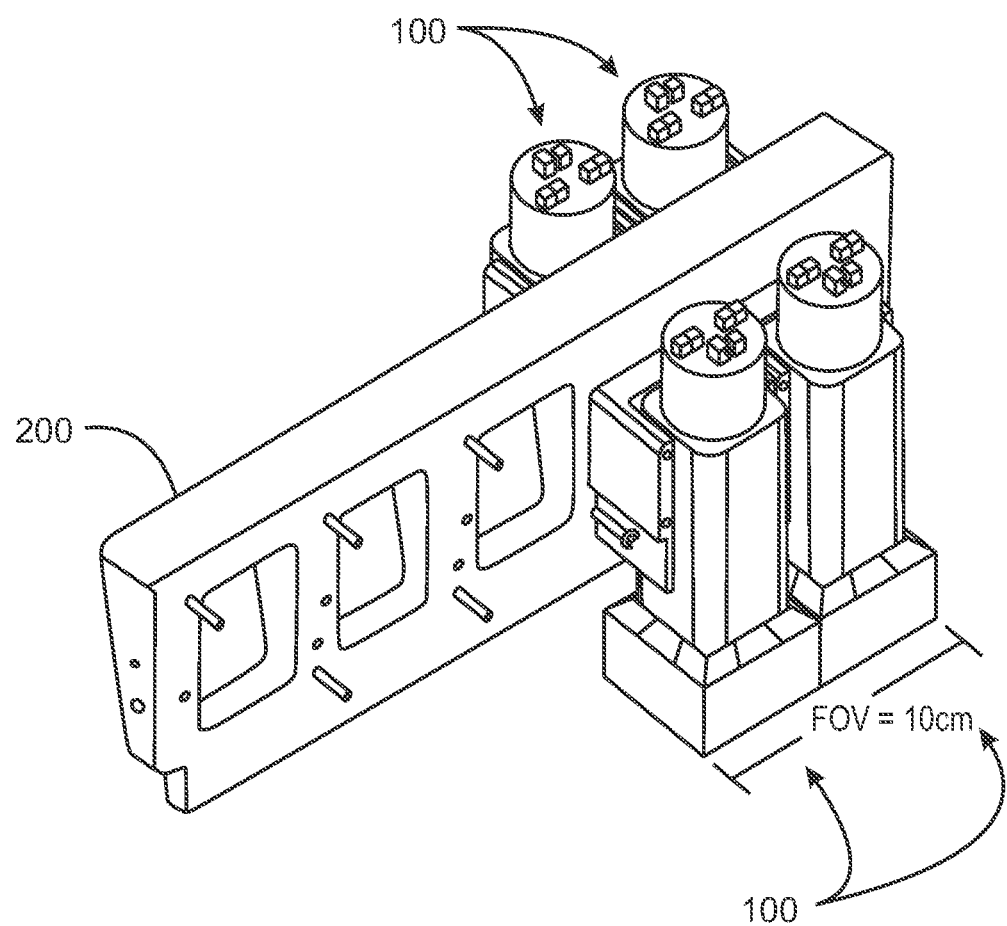
FIG. 4A is an illustration of a detector module with four detector units in accordance with embodiments.

FIG. 4A is an illustration of detector module 400A with four detector units in accordance with embodiments. In PET systems, the most expensive component may be the detector units. Accordingly, reducing the number of detector units can result in a reduction of cost of the PET system. The detector module 400A includes four detector units 100, with each detector unit having a scintillator block surface area of five by five centimeters. When multiple modules are assembled into a ring formation as in FIG. 5, this creates 2 rows of detector units in a ring, resulting in a total field of view (FOV) of ten centimeters. The FOV is a measure of the axial length that can be acquired by the PET scanner at one time. In some cases, a PET system including the detector modules such as the detector module 400 may be considered a base or entry-level PET system, as it is a system that is minimally equipped with detectors. More consumers have the funding available to enter the PET system market with a cost effective entry level configuration. In embodiments, an entry level modular system according to the present techniques will not add additional inventory due to scalability and modularity of the present techniques, while potentially opening up a new commercial market.

Figure 4B:
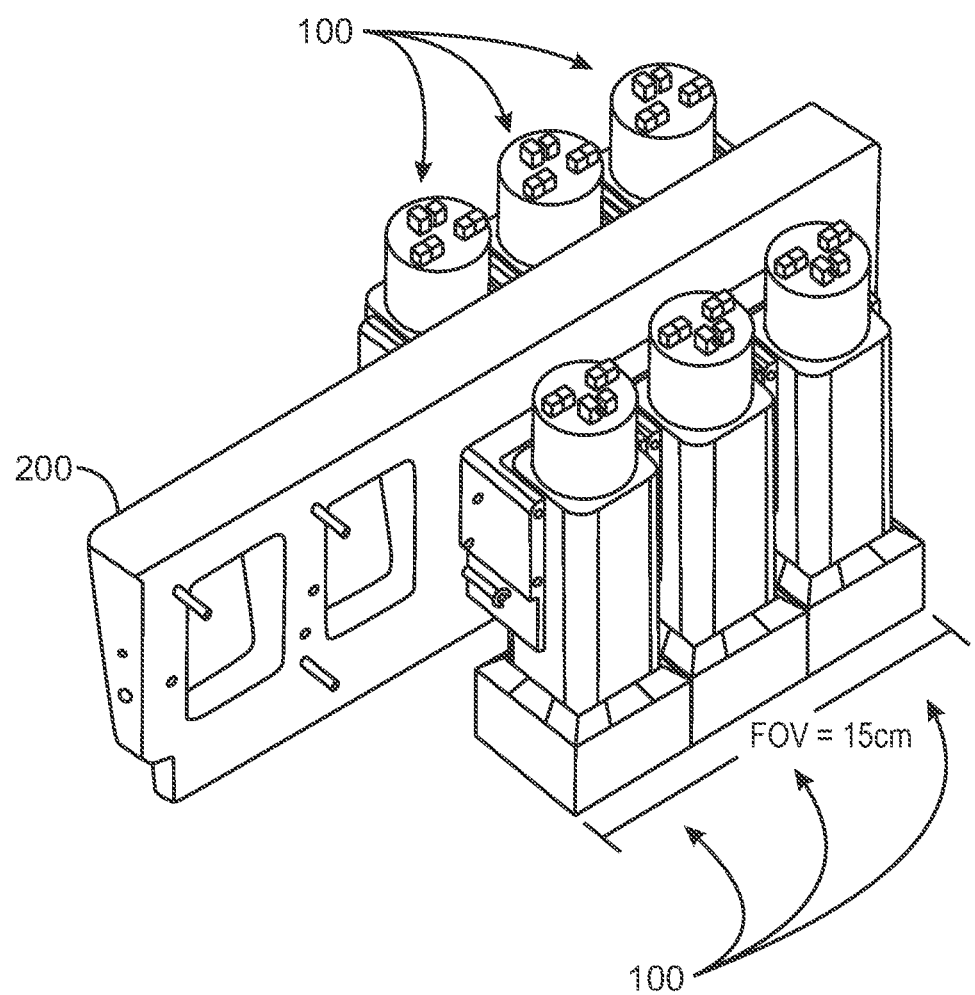
FIG. 4B is an illustration of a detector module with six detector units in accordance with embodiments.
Figure 4C:
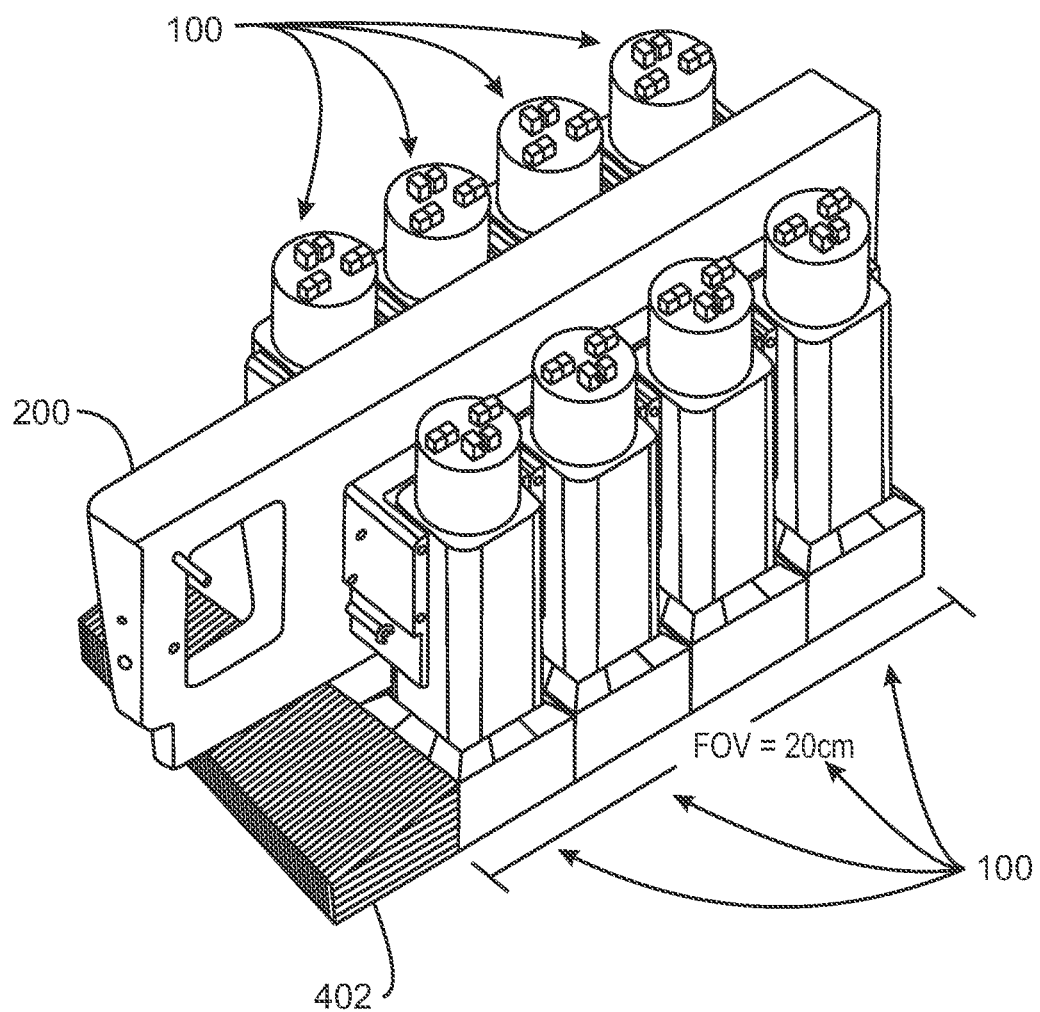
FIG. 4C is an illustration of a detector module with eight detector units in accordance with embodiments.

FIG. 4B is an illustration of detector module 400B with six detector units. A PET system including the detector module 400B may result in a FOV of fifteen centimeters. Similarly, FIG. 4C is an illustration of detector module 400C with eight detector units. A PET system including the detector module 400C may result in a FOV of twenty centimeters. Detector module 400C also includes a rear shield 402. The rear shield 402 may be implemented in any detector module in order to reduce the effect of scattered radiation from outside of the FOV. In embodiments, the rear shield is a high-density scatter shield typically made of lead.

Figure 4D:
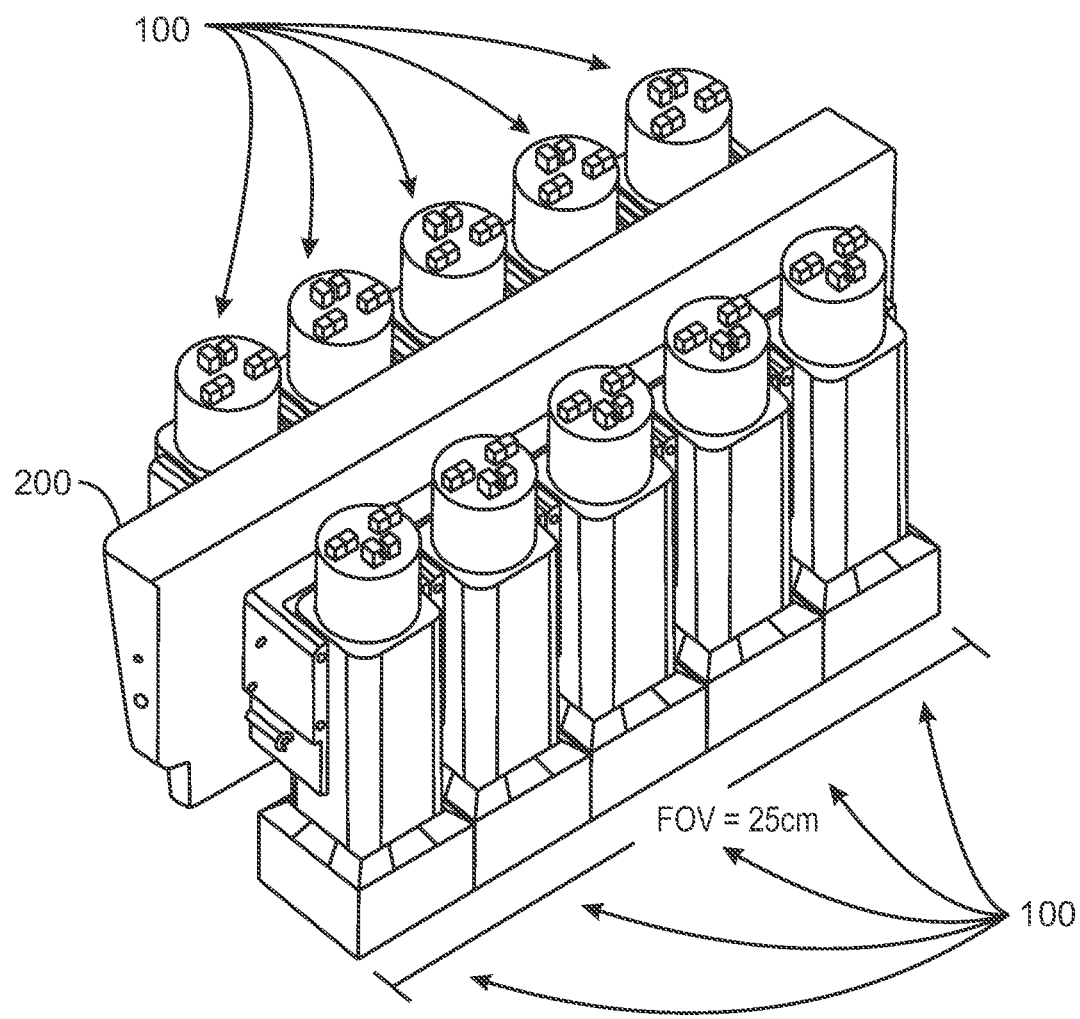
FIG. 4D is an illustration of a detector module with ten detector units in accordance with embodiments.

FIG. 4D is an illustration of detector module 400D with ten detector units. A PET system including the detector module 400D may result in a FOV of twenty-five centimeters. The detector module in each of FIGS. 4A, 4B, 4C, and 4D has a modular and scalable field of view that can be increased or decreased by the addition or removal of detectors units. As shown by FIGS. 4A-4D, multiple scanner fields of view are enabled by populating the detector frames with more or less rows of individual detectors.

The detector module configurations illustrated in FIGS. 4A, 4B, 4C, and 4D can be purchased as-is with any number of detector units. Additional detector units can be added to a modular PET-system as the consumer desires to increase or upgrade the field of view to next available system configuration. Thus, the PET system of the present techniques enables upgrades of PET systems at any time during the life cycle of the system. Traditionally, detector upgrades of systems in the field are extremely costly, requiring replacement of an entire ring or purchase of a new scanner entirely. Traditional PET scanner hardware cannot grow as a medical practice grows, however, the present techniques enable PET systems to be upgraded in the field by adding additional detector units, instead of swapping the entire ring or purchasing an entirely new scanner. Moreover, the material and labor cost of field replacement of a detector is significantly reduced when compared to traditional PET systems. Failed units can be replaced on an individual basis, whereas previously, an entire set of detectors needed to be replaced.

Figure 5:
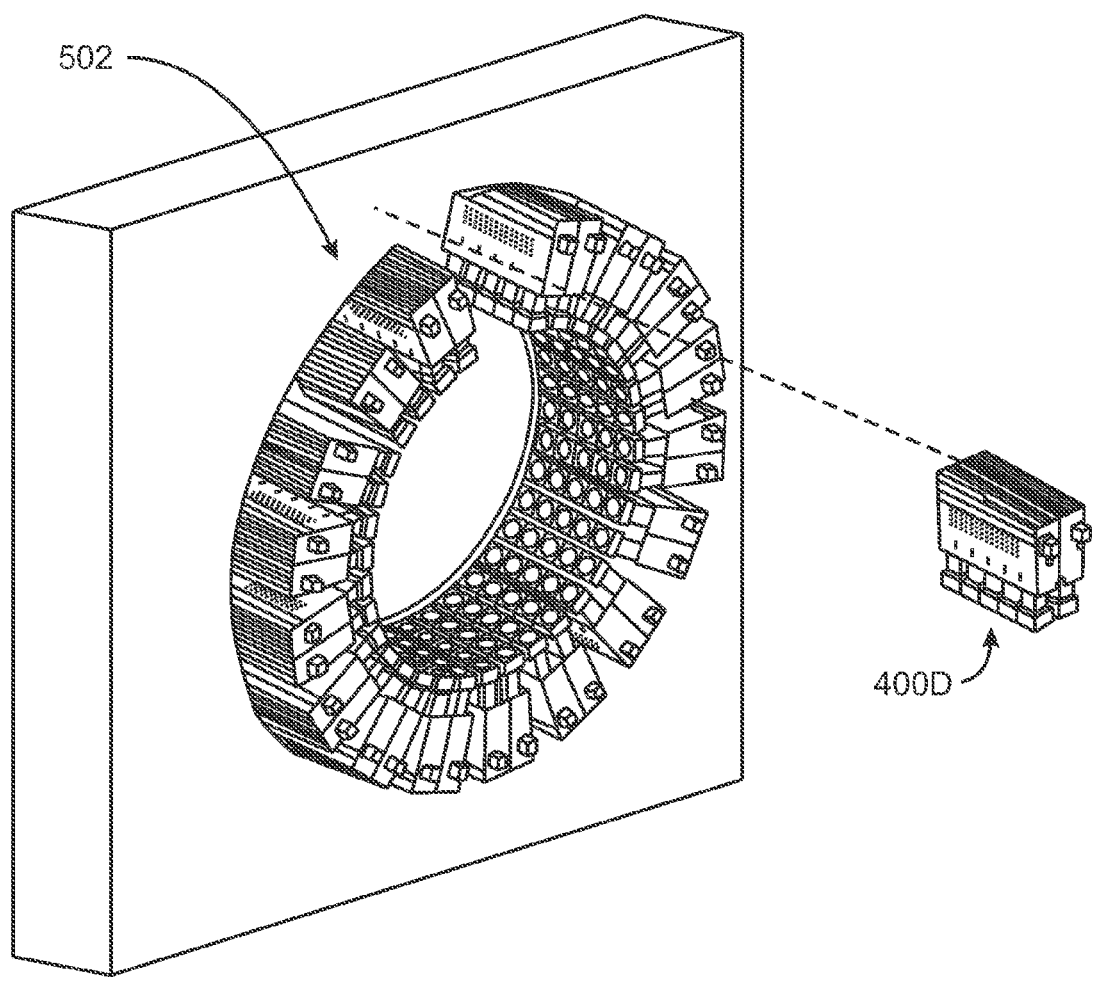
FIG. 5 is an illustration of a ring structure of a PET gantry.

FIG. 5 is an illustration of a PET gantry 500 with plurality of 400D detector modules. The PET gantry may include a plurality of detector modules 400A, 400B, 400C or 400D per system configurations, as illustrated in FIGS. 4A, 4B, 4C and 4D. In embodiments, the PET-system is coupled with CT technology resulting in a PET-CT scanner. The detector modules 400A, 400B 400C or 400D may be mounted to a common mechanical mounting structure 502 in a ring formation per system configuration. In embodiments, eighteen modules form a full ring of detector modules. If a detector unit must be removed or installed, the module it resides on is removed from the ring structure. An individual detector unit can be removed, replace, or installed, and the module is then re-installed onto the ring. The ring structure includes module mounting holes that are machined in a single machining process, thereby minimizing detector module to detector module location tolerance. This tolerance, along with the tolerance accumulated from the detector unit and the mounting frame, forms the overall system tolerance stack. By machining location features of the mounting frame 200 and the mounting structure 502 in as few steps as possible, the overall system tolerance stack is minimized.

A rear shielding of the detector is also scalable to accommodate the modular design, as illustrated in FIG. 4C. This is accomplished by using the same rear lead pieces, mounted to the appropriate axial location on the detector frame depending on the number of detector units present. The rear shielding may also be accomplished by using a configuration specific spacer, where the spacer locates the rear shield at the required axial position depending on the number of detector units present. These spacers are mounted to an external structure using screws and are easily removable or swappable. Typically, detectors are to populate the mounting frame from one side to the other, regardless of FOV configuration. For example, in FIG. 3, the right side of the mounting frame 200 is populated with detector units 100, thereby filling the mounting frame from the right to the left. Accordingly, the front side of the FOV may include a front shield that is permanently affixed to the module mounting structure 502. Since the location of the rear-most detector unit can vary based on FOV configuration, the placement of the rear shield is also scalable. Moreover, the size of the rear shield is configurable.

The block diagrams of FIGS. 1-5 are not intended to indicate that the modular PET gantry is to include all of the components shown in FIGS. 1-5 in every case. Moreover, any number of additional or alternative components not shown in FIGS. 1-5 may be included in the detector module, depending on the details of the specific implementation. For example, the detector module may also include cables, circuitry, and various other hardware components to electrically couple the detector units with a computing device. Moreover, although a detector unit is described, the detector unit may also be a silicon photomultiplier (SiPM) based detector unit.

Figure 6:
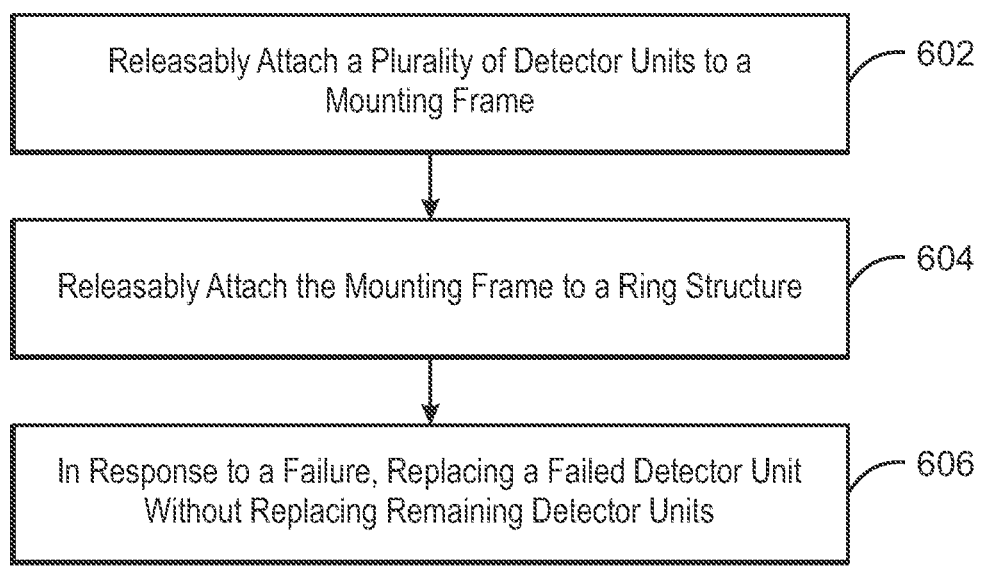
FIG. 6 is a process flow diagram of a method for assembling a modular PET system.

FIG. 6 is a process flow diagram of a method 600 for assembling a modular PET system. At block 602, a plurality of detector units are releasably attached to a mounting frame. In embodiments, the detector unit includes a scintillator block, a PMT tube, a light guide, and a mounting sleeve. The mounting sleeve may be used to attach the detector unit to the mounting frame. The addition of a light guide to a scintillator block and PMT combination enables a ratio between a width of the scintillator block and a width PMT tube to be increased without the loss of any light from the scintillator block as it is acquired by the PMT. The reduction in the width of the PMT enables additional hardware, such as the mounting sleeve to be bonded around the scintillator block and PMT combination. The hardware creates a modular PET system, where individual detector units can be removed of replaced in the event of a detector unit failure.

At block 604, the mounting frame is attached to a ring structure. Further, at block 606, in response to failure of a detector unit, the failed detector unit is replaced without replacing other detector units releasably attached to the mounting frame. This modular PET system results in a significant reduction in the cost of field replacement of detectors. Traditionally, the replacement of failed detectors in the field is expensive, relatively common, and requires replacing entire sets of detectors. The present techniques enable replace of a single, individual detector unit, rather than an entire detector that includes multiple detector units permanently mounted together. Moreover, material wasted from replacing detector units that have not failed is reduced, as well as the intensive labor to replace multiple detector units permanently mounted together is reduced.

The process flow diagram of FIG. 6 is not intended to indicate that the blocks of the method 600 are to be executed in any particular order, or that all of the blocks shown in FIG. 6 are to be included in every case. Furthermore, the method 600 may include any number of additional or alternative blocks not shown in FIG. 6, depending on the details of the specific implementation.

The present techniques enable a reduction in the cost of managing multiple products for multiple customer segments, as the modular and scalable field of view provides multiple product configurations that can be targeted at different markets, all on the same platform. This results in a flexible and lean inventory that adequately meets the demand for PET systems. Further, generic gantries can be stocked that are easily converted to any of the product configurations on-demand by the addition or removal of detector units, which significantly reduces inventory. Moreover, the lower levels of system configurations can be upgraded at any time. This upgradeability enables the sale of value-end PET scanners with the option to upgrade the hardware later to a higher-performance machine to recognize additional revenue. In this manner, the customer can upgrade the PET system to a larger field of view at the customer site in a short amount of time. Additionally, a cost barrier to entry into the PET scanner services market is reduced and possibly eliminated, as the detector units are the most expensive part of the system and a significant number of them are used in a standard PET scanner which can make any PET scanner prohibitively expensive for some consumers.

While embodiments are described herein with respect to detector units used in the medical field, embodiments described herein can encompass those situations in which any detector unit is precisely located in a detector module. Further, those of skill in the art will recognize that the present techniques are applicable to many different hardware configurations, software architectures, organizations, or processes.

While the detailed drawings and specific examples given describe particular embodiments, they serve the purpose of illustration only. The systems and methods shown and described are not limited to the precise details and conditions provided herein. Rather, any number of substitutions, modifications, changes, and/or omissions may be made in the design, operating conditions, and arrangements of the embodiments described herein without departing from the spirit of the present techniques as expressed in the appended claims.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:
1. A detector module, comprising:
   a scintillator block having a block width;
   a tube coupled to the scintillator block and configured to acquire light from the scintillator block, the tube having an external tube width;

a mounting sleeve configured to accept the tube, the mounting sleeve having a sleeve width, wherein the sleeve width and the external tube width are less than the block width;
- a plurality of PET detector units, wherein each detector unit is bonded to the mounting sleeve;
- a light guide, wherein the light guide guides scintillations from the scintillator block to the tube of the detector unit; and
- a mounting frame, wherein each detector unit and mounting sleeve are attached to the mounting frame.

2. The detector module of claim 1, wherein an aspect ratio of the block width to the external tube width is at least four-to-three.

3. The detector module of claim 1, wherein the mounting sleeve attaches the detector unit to the mounting frame.

4. The detector module of claim 1, wherein the mounting sleeve includes at least one pin hole, at least one screw hole, or any combination thereof.

5. The detector module of claim 1, wherein the detector unit is a field replaceable unit.

6. The detector module of claim 1, wherein the mounting sleeve is attached to the mounting frame via an alignment pin, a locking screw, a rail mechanism, or any combination thereof.

7. The detector module of claim 1, wherein a rear shield is mounted to the frame to enable sufficient rear end shielding from radioactive scatter outside a field of view.

8. The detector module of claim 1, wherein the detector module is mounted to a common mechanical mounting structure in a ring formation.

9. The detector module of claim 1, wherein each detector unit is bonded to a mounting sleeve using a gluing fixture.

10. A detector unit, comprising:
- a detection tube having an external tube width;
- a mounting sleeve configured to accept the tube, the mounting sleeve having a sleeve width, the mounting sleeve comprising mounting features configured to enable location of the detector unit;
- a scintillator block having a block width that is greater than the sleeve width and the external tube width, wherein a light guide guides scintillations from the scintillator block to the detection tube.

11. The detector unit of claim 10, wherein an aspect ratio of the block width to the external tube width is at least four-to-three.

12. The detector unit of claim 10, wherein the mounting sleeve enables precision molded connections to a mounting frame, machined pin hole connections to a mounting frame, or any combination thereof.

13. The detector unit of claim 10, wherein the detection tube is a photomultiplier tube.

14. The detector unit of claim 10, wherein the detector unit is a silicon photomultiplier based detector unit.

15. The detector unit of claim 10, wherein the light guide enables transfer of light from scintillator to the detector tube.

16. A modular PET system, comprising:
- a plurality of detector modules, wherein the detector modules are arranged in a ring and each detector module comprises:
  - a plurality of PET detector units each comprising a scintillator block having a block width, a tube having an external tube width, and a mounting sleeve having a sleeve width, the tube configured to acquire light from the scintillator block, the mounting sleeve configured to accept the tube, wherein each detector unit is bonded to a corresponding mounting sleeve, the sleeve width and the external tube width less than the block width;
  - a plurality of light guides, wherein each light guide enables photons from a scintillator block to travel to a tube of its respective detector unit; and
  - a mounting frame, wherein each detector unit and mounting sleeve are attached to the mounting frame, wherein neighboring detector units are oriented in a common direction with neighboring scintillator blocks adjacent to one another.

17. The system of claim 16, wherein the plurality of detector modules are to be arranged in a ring by mounting the plurality of detector modules to a common mechanical mounting structure in a ring formation.

18. The system of claim 16, wherein the plurality of detector modules are arranged in a ring by mounting the plurality of detector modules to a common mechanical mounting structure in a ring formation, wherein the a plurality of mounting holes of the plurality of mounting sleeves in the ring are machined in a single process to minimize module-to-module location tolerance.

19. The system of claim 16, comprising a rear shield located in an appropriate axial location, wherein the rear shield is scalable to a number of detector units.

20. The system of claim 16, wherein each detector module of the plurality of detector modules can be replaced.

\* \* \* \* \*